United States Patent [19]

Petersen et al.

[11] Patent Number: 4,563,448

[45] Date of Patent: Jan. 7, 1986

[54] BACTERICIDAL AGENTS

[75] Inventors: Uwe Petersen, Leverkusen; Klaus Grohe, Odenthal; Karl-Heinz Kuck, Langenfeld, all of Fed. Rep. of Germany

[73] Assignee: Bayer Aktiengesellschaft, Leverkusen, Fed. Rep. of Germany

[21] Appl. No.: 585,811

[22] Filed: Mar. 2, 1984

[30] Foreign Application Priority Data

Mar. 12, 1983 [DE] Fed. Rep. of Germany ....... 3308908

[51] Int. Cl.$^4$ .................. A61K 31/555; A61K 31/50; A61K 31/495; C07F 1/00
[52] U.S. Cl. .................................... 514/187; 514/252; 544/225
[58] Field of Search ................ 544/225; 424/250, 245; 514/187, 252

[56] References Cited

U.S. PATENT DOCUMENTS

| | | | |
|---|---|---|---|
| 4,359,578 | 11/1982 | Matsumoto et al. | 424/250 |
| 4,398,029 | 8/1983 | Irikura et al. | 424/250 |
| 4,404,197 | 9/1983 | Fox, Jr. et al. | 424/250 |
| 4,429,127 | 1/1984 | Irikura et al. | 424/250 |

FOREIGN PATENT DOCUMENTS

| | | | |
|---|---|---|---|
| 1141383 | 2/1983 | Canada | 424/250 |
| 0000203 | 7/1981 | European Pat. Off. | |
| 0049593 | 4/1982 | European Pat. Off. | 424/245 |
| 0049355 | 4/1982 | European Pat. Off. | |
| 0058614 | 8/1982 | European Pat. Off. | 424/250 |
| 3106013 | 9/1982 | Fed. Rep. of Germany | 424/250 |
| 2449682 | 9/1980 | France | |
| 2496663 | 6/1982 | France | 424/250 |
| 2030562A | 4/1980 | United Kingdom | |
| 2057440A | 4/1981 | United Kingdom | |

Primary Examiner—Albert T. Meyers
Assistant Examiner—Joyce L. Morrison
Attorney, Agent, or Firm—Sprung Horn Kramer & Woods

[57] ABSTRACT

A method of combating plant-pathogenic bacteria, comprising applying to the bacteria or to a bacteria habitat a bactericidally effective amount of a cyclopropyl-1,4-dihydro-4-oxo-3-quinolinecarboxylic acid derivative of the formula

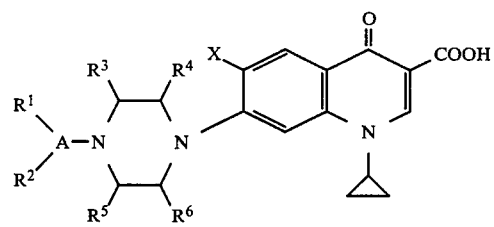

in which
A represents straight-chain or branched alkylene with 1 to 6 carbon atoms or a >C=CH— radical,
$R^1$ represents alkoxycarbonyl with 1 to 6 carbon atoms in the alkyl part, benzyloxycarbonyl, carboxyl, optionally substituted carbamoyl, cyano or dialkoxyphosphonyl or alkylsulphonyl with 1 to 4 carbon atoms in the alkyl part, and
$R^2$ represents hydrogen, alkoxycarbonyl with 1 to 6 carbon atoms in the alkyl part, benzyloxycarbonyl, optionally substituted carbamoyl, cyano, chlorine, acetyl, alkyl with 1 to 3 carbon atoms or phenyl, or
$R^1$ and $R^2$, together with the carbon atom which they substitute, can also form a 2-oxo-tetrahydrofuryl ring,
$R^3$, $R^4$, $R^5$ and $R^6$ can be identical or different and represent hydrogen, methyl, ethyl or n- or i-propyl and
X represents hydrogen, halogen or nitro,
or an acid addition salt, alkali metal salt, alkaline earth metal salt, heavy metal salt or hydrate thereof. The heavy metal salts are new.

12 Claims, No Drawings

BACTERICIDAL AGENTS

The present invention relates to the use of quinolonecarboxylic acids as antibacterial agents.

Certain 1-cyclopropyl-1,4-dihydro-4-oxo-3-quinolinecarboxylic acids, such as, for example, 1-cyclopropyl-6-fluoro-1,4-dihydro-4-oxo-7-(1-piperazinyl)-3-quinolinecarboxylic acid, are already known (compare European Patent Specification No. 49,355). Nothing is known of a microbicidal action in the plant protection sector, only their use in the pharmaceutical sector is known.

It has furthermore been disclosed that certain quinolonecarboxylic acid derivatives, such as, for example, 7-chlor-1-ethyl-6-fluoro-1,4-dihydro-4-oxo-3-quinolinecarboxylic acid, have a bactericidal action in the plant protection sector (compare European Patent Application No. 0,203). However, the activity is not always satisfactory when low concentrations are applied.

It has been found that the new quinolonecarboxylic acids of the formula (I)

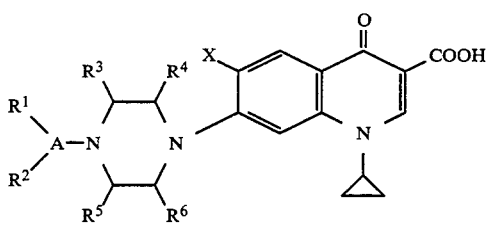

in which

A represents straight-chain or branched alkylene with 1 to 6 carbon atoms or a $>C=CH-$ radical, $R^1$ represents alkoxycarbonyl with 1 to 6 carbon atoms in the alkyl part, benzyloxycarbonyl, carboxyl, optionally substituted carbamoyl, cyano or dialkoxyphosphonyl or alkylsulphonyl with 1 to 4 carbon atoms in the alkyl part and $R^2$ represents hydrogen, alkoxycarbonyl with 1 to 6 carbon atoms in the alkyl part, benzyloxycarbonyl, optionally substituted carbamoyl, cyano, chlorine, acetyl, alkyl with 1 to 3 carbon atoms or phenyl, or $R^1$ and $R^2$, together with the carbon atom to which they are bonded, can also form a 2-oxo-tetrahydrofuryl ring, $R^3$, $R^4$, $R^5$ and $R^6$ can be identical or different and represent hydrogen, methyl, ethyl or n- or i-propyl and X represents hydrogen, halogen, preferably fluorine or chlorine, or nitro, and acid addition salts, alkali metal salts, alkaline earth metal salts, heavy metal salts and hydrates thereof, have bactericidal properties.

Surprisingly, the quinolonecarboxylic acids of the formula (I) which can be used according to the invention exhibit a more powerful bactericidal activity than the quinolonecarboxylic acid from the prior art which is most closely related chemically and from the point of view of its action, that is to say 7-chloro-1-ethyl-6-fluoro-1,4-dihydro-4-oxo-3-quinolonecarboxylic acid. The new use of the compounds according to the invention thus represents an enrichment of the art.

Formula (I) provides a general definition of the compounds which can be used according to the invention.

Those compounds of the formula (I) in which

A represents straight-chain or branched alkylene with 1 to 5 carbon atoms or the $>C=CH-$ group, $R^1$ represents alkoxycarbonyl with 1 to 5 carbon atoms in the alkyl part, benzyloxycarbonyl, carboxyl, carbamoyl which is optionally substituted by 1 or 2 methyl or ethyl radicals, cyano, methylsulphonyl or ethylsulphonyl and $R^2$ represents hydrogen, alkoxycarbonyl with 1 to 5 carbon atoms in the alkyl part, benzyloxycarbonyl, carbamoyl, cyano, chlorine, acetyl, alkyl with 1 or 2 carbon atoms or phenyl, or $R^1$ and $R^2$, together with the carbon atom which they substitute, can also form a 2-oxo-tetrahydrofuryl ring, $R^3$, $R^4$, $R^5$ and $R^6$ represent hydrogen, methyl or ethyl and X represents hydrogen, fluorine, chlorine or nitro, are preferably used.

Those compounds of the formula (I) in which

A represents straight-chain alkylene with 1 to 5 carbon atoms or the $>C=CH-$ group, $R^1$ represents alkoxycarbonyl with 1 to 4 carbon atoms in the alkyl part, benzyloxycarbonyl, carboxyl, carbamoyl, cyano or methylsulphonyl and $R^2$ represents hydrogen, alkoxycarbonyl with 1 to 3 carbon atoms in the alkyl part, cyano, chlorine, acetyl or phenyl, or $R^1$ and $R^2$, together with the carbon atom which they substitute, can also form a 2-oxo-tetrahydro-3-furyl ring, $R^3$ represents hydrogen, methyl or ethyl,
$R^4$ represents hydrogen,
$R^5$ represents hydrogen or methyl,
$R^6$ represents hydrogen and X represents hydrogen, fluorine, chlorine or nitro, are particularly preferably used.

If appropriate, the compounds of the formula (I) which can be used according to the invention can be converted into a salt with an organic or inorganic acid. Examples of suitable acids for salt formation are the hydrogen halides acids, such as hydrochloric acid, hydrobromic acid and hydriodic acid, and furthermore sulphuric acid, acetic acid, citric acid, ascorbic acid, methanesulphonic acid and benzenesulphonic acid. Preferred suitable alkali metal and alkaline earth metals salts are the sodium, potassium, calcium and magnesium salts, and preferred suitable heavy metal salts are the copper, zinc and manganese salts.

Possible anions of these salts are those which are derived from acids leading to physiologically acceptable addition products. In this connection, particularly preferred acids of this type are the hydrogen halide acids, such as, for example, hydrochloric acid and hydrobromic acid, and nitric acid and sulphuric acid.

New active compounds which can be used antibacterially and which may be mentioned specifically are: 7-[4-(methoxycarbonylmethyl)-1-piperazinyl]-1-cyclopropyl-6-fluoro-1,4-dihydro-4-oxo-3-quinolinecarboxylic acid, 7-[4-(ethoxycarbonylmethyl)-1-piperazinyl]-1-cyclopropyl-6-fluoro-1,4-dihydro-4-oxo-3-quinolinecarboxylic acid, 7-[4-(2-benzyloxycarbonylethyl)-1-piperazinyl]-1-cyclopropyl-6-fluoro-1,4-dihydro-4-oxo-3-quinolinecarboxylic acid, 7-[4-(5-benzyloxycarbonylpentyl)-1-piperazinyl]-1-cyclopropyl-6-fluoro-1,4-dihydro-4-oxo-3-quinolinecarboxylic acid, 7-[4-(2-methoxycarbonylethyl)-1-piperazinyl]-1-cyclopropyl-6-fluoro-1,4-dihydro-4-oxo-3-quinolinecarboxylic acid, 7-[4-(2-ethoxycarbonylethyl)-1-piperazinyl]-1-cyclopropyl-6-fluoro-1,4-dihydro-4-oxo-3- quinolinecarboxylic acid, 7-[4-(2-propoxycarbonyle-thyl)-1-piperazinyl]-1-cyclopropyl-6-fluoro-1,4-dihydro-4-oxo-3-quinolinecarboxylic acid, 7-[4-(2-n-butoxycarbonylethyl)-1-piperazinyl]-1-cyclopropyl-6-fluoro-1,4-dihydro-4-oxo-3-quinolinecarboxylic acid, 7-[4-(2-cyanoethyl)-1-piperazinyl]-1-cyclopropyl-6-fluoro-1,4-dihydro-4-oxo-3-quinolinecarboxylic acid, 7-[4-(3-cyanopropyl)-1-piperazinyl]-1-cyclopropyl-6-fluoro-1,4-dihydro-4-oxo-3-quinoline-carboxylic acid, 7-{4-[α-(benzyloxycarbonyl)-benzyl]-1-piperazinyl}-1-cyclopropyl-6-fluoro-1,4-dihydro-4-oxo-3-quinolinecarboxylic acid, 7-[4-carbamoylmethyl-1-piperazinyl]-1-cyclopropyl-6-fluoro-1,4-dihydro-4-oxo-3-quinolinecarboxylic acid, 7-[4-cyanomethyl-1-piperazinyl]-1-cyclopropyl-6-fluoro-1,4-dihydro-4-oxo-3-quinolinecarboxylic acid, 7-[4-(N-methylcarbamoylmethyl)-1-piperazinyl]-1-cyclopropyl-6-fluoro-1,4-dihydro-4-oxo-3-quinolinecarboxylic acid, 7-[4-(N-ethylcarbamoylmethyl)-1-piperazinyl]-1-cyclopropyl-6-fluoro-1,4-dihydro-4-oxo-3-quinolinecarboxylic acid, 7-{4-[2-oxo-1-(methoxycarbonyl)-1-propyl]-1-piperazinyl}-1-cyclopropyl-6-fluoro-1,4-dihydro-4-oxo-3-quinolinecarboxylic acid, 7-[4-(2-oxo-tetrahydrofuryl-3-)-1-piperazinyl]-1-cyclopropyl-6-fluoro-1,4-dihydro-4-oxo-3-quinolinecarboxylic acid, 7-[4-(carboxymethyl)-1-piperazinyl]-1-cyclopropyl-6-fluoro-1,4-dihydro-4-oxo-3-quinolinecarboxylic acid, 7-[4-(2-carboxyethyl)-1-piperazinyl]-1-cyclopropyl-6-fluoro-1,4-dihydro-4-oxo-3-quinolinecarboxylic acid, 7-[-4-(2-carboxypropyl)-1-piperazinyl]-1-cyclopropyl-6-fluoro-1,4-dihydro-4-oxo-3-quinolinecarboxylic acid, 7-[4-(3-carboxypropyl)-1-piperazinyl]-1-cyclopropyl-6-fluoro-1,4-dihydro-4-oxo-3-quinolinecarboxylic acid, 7-[4-(5-carboxypentyl)-1-piperazinyl]-1-cyclopropyl-6-fluoro-1,4-dihydro-4-oxo-3-quinolinecarboxylic acid, 7-[4-(α-carboxybenzyl)-1-piperazinyl]-1-cyclopropyl-6-fluoro-1,4-dihydro-4-oxo-3-quinolinecarboxylic acid, 7-[4-(2-chloro-2-cyanoethyl)-1-piperazinyl]-1-cyclopropyl-6-fluoro-1,4-dihydro-4-oxo-3-quinolinecarboxylic acid, 7-[4-(2-methylsulphonyl-ethyl)-1-piperazinyl]-1-cyclopropyl-6-fluoro-1,4-dihydro-4-oxo-3-quinolinecarboxylic acid, 7-[4-(2-diethoxyphosphonylethyl)-1-piperazinyl]-1-cyclopropyl-6-fluoro-1,4-dihydro-4-oxo-3-quinolinecarboxylic acid, 7-[4-(2-methoxycarbonylethyl)-1-piperazinyl]-1-cyclopropyl-1,4-dihydro-6-nitro-4-oxo-3-quinolinecarboxylic acid, 7-[4-(2-methoxycarbonylethyl)-1-piperazinyl]-6-chloro-1-cyclopropyl-1,4-dihydro-4-oxo-3-quinolinecarboxylic acid, 7-[4-(2-methoxycarbonylethyl)-1-piperazinyl]-1-cyclopropyl-1,4-dihydro-4-oxo-3-quinolinecarboxylic acid, 7-[4-(2-benzyloxycarbonylethyl)-3-methyl-1-piperazinyl]-1-cyclopropyl-6-fluoro-1,4-dihydro-4-oxo-3-quinolinecarboxylic acid and 7-[4-(2-methoxycarbonylethyl)-3,5-dimethyl-1-piperazinyl]-1-cyclopropyl-6-fluoro-1,4-dihydro-4-oxo-3-quinolinecarboxylic acid.

As discussed, these compounds of the formula (I) which can be used according to the invention can be converted, if appropriate, into a salt with an organic or inorganic acid. Acids which are suitable for salt formation are the hydrogen halide acids already mentioned, such as hydrochloric acid, hydrobromic acid and hydriodic acid, and furthermore sulphuric acid, acetic acid, citric acid, ascorbic acid and benzenesulphonic acid. Preferred suitable alkali metal salts and alkaline earth metal salts are the sodium, potassium, calcium and magnesium salts, and preferred suitable heavy metal salts are the copper, zinc and manganese salts.

The active compounds to be used according to the invention are the subject of Application Ser. No. 576,596, filed Feb. 3, 1984, now pending.

They are obtained by reacting a compound of the formula (II)

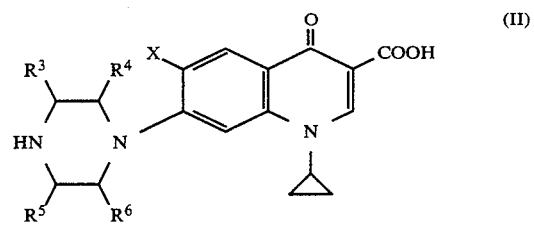

in which X, $R^3$, $R^4$, $R^5$ and $R^6$ have the abovementioned meaning, with a compound of the formula (III)

in which $R^1$, $R^2$ and A have the abovementioned meaning and Y represents halogen, preferably chlorine, bromine or iodine, $CH_3O-SO_2-O-$, $C_2H_5O-SO_2-O-$, methoxy or ethoxy (method A). Compounds of the formula (I) which can be used according to the invention are also obtained by reacting compounds of the formula (II)

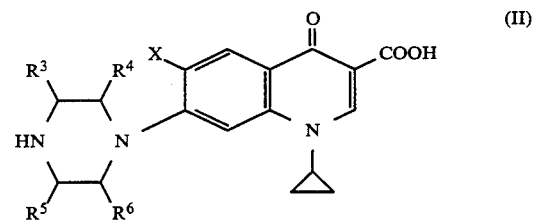

with compounds of the formula (IV)

in which $R^1$ and $R^2$ have the abovementioned meaning, compounds of the formula (Ia)

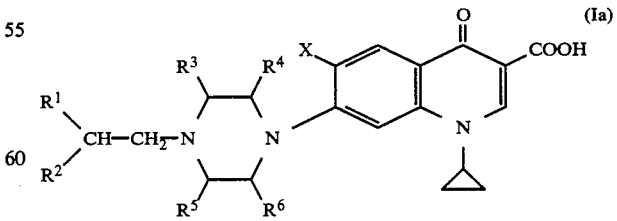

which can be used according to the invention being formed (method B).

Compounds of the formula (I) which can be used according to the invention are also obtained by reacting compounds of the formula (V)

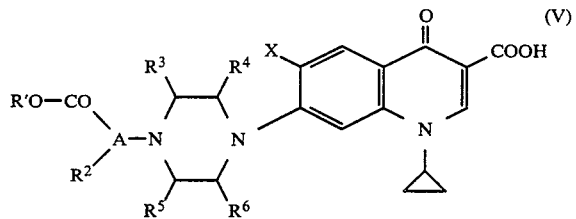

in which

R², R³, R⁴, R⁵, R⁶ and X have the abovementioned meaning and

R' represents alkyl with 1 to 6 carbon atoms or benzyl, under alkaline or acid conditions or, if R' represents benzyl, also under hydrogenolytic conditions, compounds of the formula (Ib)

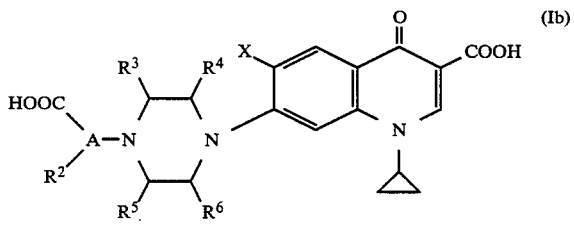

in which R², R³, R⁴, R⁵, R⁶ and X have the abovementioned meaning, which can be used according to the invention, being formed (method C).

The compounds of the formula (II) to be used as starting compounds can be prepared by reacting compounds of the formula (VI)

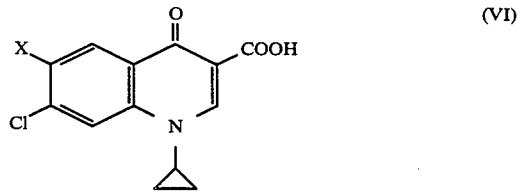

with piperazine or piperazine derivatives of the formula (VII)

This reaction is carried out in a diluent, such as, for example, dimethylsulphoxide, hexamethylphosphoric acid trisamide, sulpholane, water, an alcohol or pyridine, at temperatures of 20° to 200° C., preferably at 80° to 180° C. In carrying out the process, 1 to 15 moles of the compound (VII), preferably 1 to 6 moles of the compound (VII), are employed per mole of carboxylic acid (VI). If equivalent amounts of the carboxylic acid (VI) and the piperazine derivative (VII) are used, the reaction is carried out in the presence of an acid-binding agent, for example triethylamine, 1,4-diaza-bicyclo[2,2,-2]octane or 1,8-diaza-bicyclo[5,4,0]undec-7-ene.

The 7-chloro-1-cyclopropyl-6-fluoro-1,4-dihydro-4-oxo-3-quinolinecarboxylic acid of the formula (VIa) (VI; X=F) used as an intermediate can be prepared in accordance with the following equation:

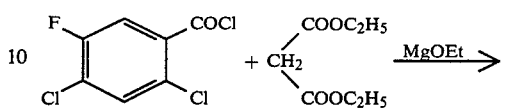

(1)  (2)

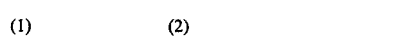

(3)

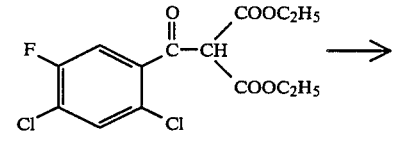

(4)

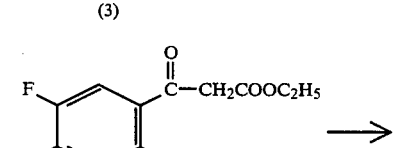

(5)

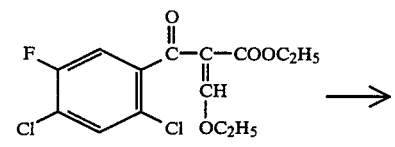

(6)

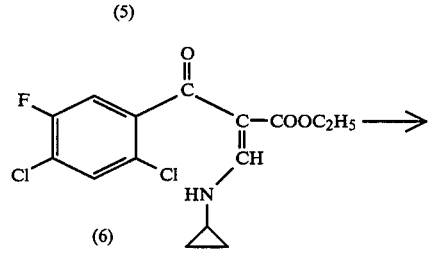

(7)

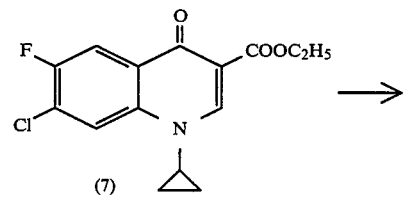

(VIa)

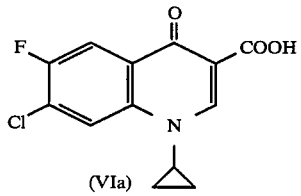

According to this equation, diethylmalonate (2) is acylated with 2,4-dichloro-5-fluoro-benzoyl chloride (1) in the presence of magnesium alcoholate (German Patent Application No. 3 142 856.8) to give the acylmalonate (3) (Organikum, 3rd edition, 1964, page 438).

Partial hydrolysis and decarboxylation of (3) in an aqueous medium with catalytic amounts of p-toluene-sulphonic acid gives a good yield of the ethyl aroylacetate (4), which is converted into ethyl 2-(2,4-dichloro-5-fluoro-benzoyl)-3-ethoxy-acrylate (5) with o-formic acid triethyl ester/acetic anhydride. The reaction of (5) with cyclopropylamine in a solvent, such as, for example, methylene chloride, alcohol, chloroform, cyclohexane or toluene, leads to the desired intermediate (6) in a slightly exothermic reaction.

The cyclization reaction (6)→(7) is carried out in a temperature range from about 60° to 280° C., preferably at 80° to 180° C.

Diluents which can be used are dioxane, dimethyl-sulphoxide, N-methyl-pyrrolidone, sulpholane, hexamethylphosphoric acid triamide and, preferably, N,N-dimethylformamide.

Possible acid-binders for this reaction stage are potassium tert.-butanolate, butyl-lithium, lithium-phenyl, phenyl-magnesium bromide, sodium methylate, sodium hydride and, particularly preferably, potassium carbonate or sodium carbonate. It may be advantageous to use an excess of 10 mole % of base.

The ester hydrolysis of (7) under basic or acid conditions effected in the last step leads to 7-chloro-1-cyclopropyl-6-fluoro-1,4-dihydro-4-oxo-3-quinolinecarboxylic acid VIa.

The 2,4-dichloro-5-fluoro-benzoyl chloride (1) used as the starting material for this synthesis route and the corresponding carboxylic acid, as well as the 3-fluoro-4,6-dichlorotoluene (10) required for preparation of (1), are prepared in accordance with the following equation, starting from 2,4-dichloro-5-methyl-aniline (8).

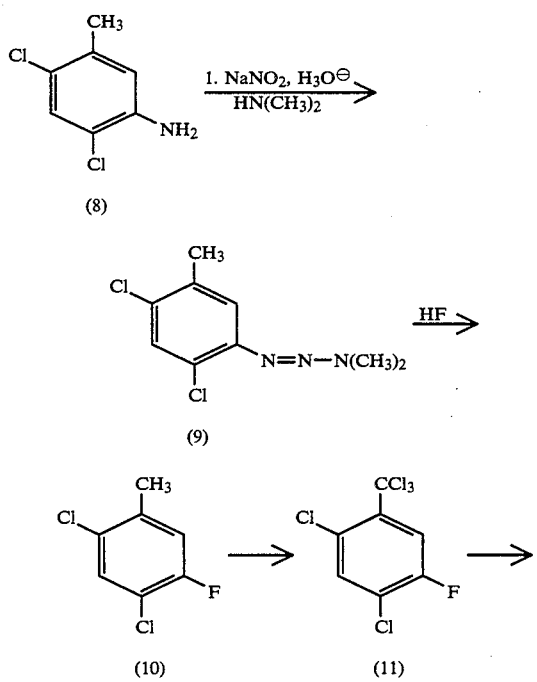

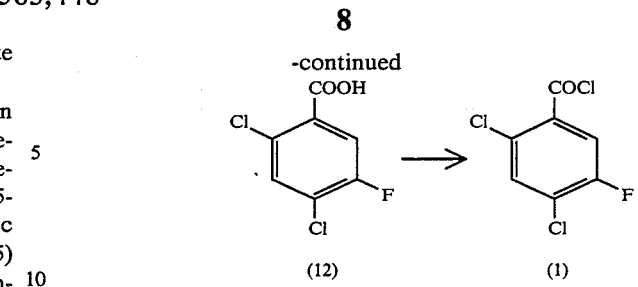

According to this equation, 2,4-dichloro-5-methylaniline (8) is diazotized with the aid of NaNO$_2$, and the diazonium salt thereby formed is converted into the triazene (9) with dimethylamine.

The triazene (9) is dissolved in excess anhydrous hydrofluoric acid. The triazene thereby splits into 2,4-dichloro-5-methyl-diazonium fluoride and dimethylamine. This solution is split into 3-fluoro-4,6-dichlorotoluene (10) under the influence of heat at 130°-140° C., with nitrogen being split off. Yield: 77% of theory.

The 3-fluoro-4,6-dichlorotoluene (10) is chlorinated in a temperature range from 110° to 160° C., under irradiation with UV light, to give 2,4-dichloro-5-fluoro-1-trichloromethylbenzene (11).

Hydrolysis of (11) with 95% strength sulphuric acid leads to 2,4-dichloro-5-fluoro-benzoic acid (12), which is converted into the carboxylic acid chloride (1) (boiling point 121°/20 mbar; n$_D^{20}$ 1.5722) with thionyl chloride.

The following quinolonecarboxylic acids used as intermediates are prepared in an analogous manner: 7-chloro-1-cyclopropyl-1,4-dihydro-4-oxo-3-quinolinecarboxylic acid (VIb) (melting point 308° C.) from 2,4-dichlorobenzoyl chloride (J. Chem. Soc. 83, 1213 (1903));

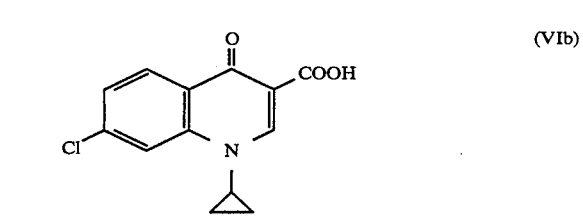

6,7-Dichloro-1-cyclopropyl-1,4-dihydro-4-oxo-3-quinolinecarboxylic acid (VIc) (melting point 265° C.) from 2,4,5-trichlorobenzoyl chloride (Liebigs Ann. Chem. 152, 238 (1869));

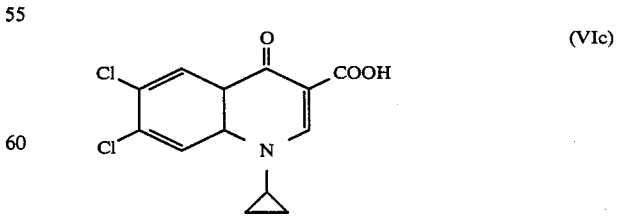

7-Chloro-1-cyclopropyl-1,4-dihydro-6-nitro-4-oxo-3-quinolinecarboxylic acid (VId) (melting point 265° to 275° C. decomposition) from 2,4-dichloro-5-nitro-benzoyl chloride (Liebigs Ann. Chem. 677, 8 (1964)).

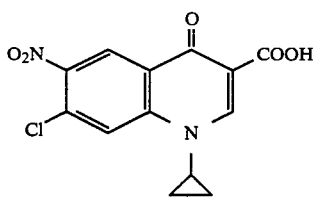

(VId)

The compounds of the formula (III) to be employed as starting substances are already known, or they can be obtained by known processes, as can the compounds of the formula (IV).

The compounds of the formula (V) which can be used according to the invention can be obtained by the methods A and B described above.

The reaction of (II) with (III) (method A) is preferably carried out in a diluent, such as dimethylsulphoxide, N,N-dimethylformamide, tetrahydrofuran, sulpholane, dioxane or pyridine, or in mixtures of these diluents, at temperatures from 0° C. to 150° C., preferably at 30° C. to 110° C.

The reaction can be carried out under normal pressure, but also under increased pressure. In general, it is carried out under pressures between about 1 and about 100 bar, preferably between 1 and 10 bar.

All the customary inorganic and organic acid-binding agents can be used as the acid-binders. These include, preferably, the alkali metal hydroxides, alkali metal carbonates, pyridine and tertiary amines, such as triethylamine and 1,4-diazabicyclo[2,2,2]octane. The reaction can be facilitated by addition of potassium iodide.

In carrying out process variant (A), 1 to 4 moles, preferably 1 to 1.5 moles, of the compound (III) are employed per mole of the compound (II).

The reaction of (II) with (IV) (method B) is preferably carried out in a diluent, such as dioxane, dimethylsulphoxide, N,N-dimethylformamide, methanol, ethanol, isopropanol, n-propanol or glycol monomethyl ether, or in mixtures of these diluents.

The reaction temperatures can be varied within a substantial range. In general, the reaction is carried out between about 20° C. and about 150° C., preferably between 50° C. and 100° C.

The reaction can be carried out under normal pressure, but also under increased pressure. In general, it is carried out under pressures between about 1 and about 100 bar, preferably between 1 and 10 bar.

In carrying out process variant (B), 1–5 moles, preferably 1–2 moles, of the compound (IV) are employed per mole of the compound (II).

The conversion of the compounds (V) into the dicarboxylic acids (Ib) (method C) is carried out either in alcoholic sodium hydroxide solution or potassium hydroxide solution or under acid conditions in mixtures of sulphuric acid or hydrochloric acid in acetic acid and/or water. The hydrogenolysis of benzyl esters (V; $R'$=benzyl) can be carried out in acetic acid in the presence of palladium catalysts.

The reaction is in general carried out at temperatures from 20° C. to 160° C., preferably at 30° to 140° C.

The reaction can be carried out under normal pressure, but also under increased pressure. In general, it is carried out under pressures between about 1 bar and about 100 bar, preferably between 1 and 10 bar.

The active compounds which can be used according to the invention exhibit a powerful microbicidal action and can be employed in practice for combating undesired microorganisms. The active compounds are suitable for use as plant protection agents.

The compounds which can be used according to the invention have a particularly powerful action against bacterial plant diseases.

Bactericidal agents are employed in plant protection for combating Pseudomonadaceae, Rhizobiaceae, Enterobacteriaceae, Corynebacteriaceae and Streptomycetaceae.

The compounds to be used according to the invention also exhibit a fungicidal action, for example against Pyricularia orycae and Pellicularia sasakii in rice.

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surfaceactive agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as methylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, with as fungicides, insecticides, acaricides and herbicides, and as mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, misting, scattering, dusting and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

Starting compounds

Example A

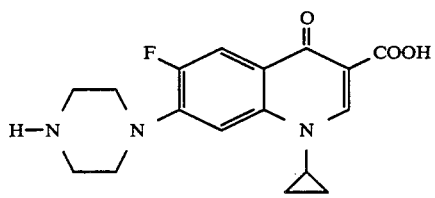

A mixture of 19.7 g of 7-chloro-1-cyclopropyl-6-fluoro-1,4-dihydro-4-oxo-3-quinolinecarboxylic acid, 30.1 g of anhydrous piperazine and 100 ml of dimethylsulphoxide is heated at 135° to 140° C. for 2 hours. The solvent is distilled off under a fine vacuum and the residue is suspended in $H_2O$, filtered off with suction and washed with water. For further purification, the moist crude product is boiled up with 100 ml of water, filtered off with suction at room temperature, washed with $H_2O$ and dried to constant weight at 100° C. over $CaCl_2$ in a vacuum drying cabinet. 19.6 g of 1-cyclopropyl-6-fluoro-1,4-dihydro-4-oxo-7-(1-piperazinyl)-3-quinolinecarboxylic acid of decomposition point 255° to 257° C. are obtained;

The 7-chloro-1-cyclopropyl-6-fluoro-1,4-dihydro-4-oxo-3-quinolinecarboxylic acid VIa used as the starting material is prepared as follows:

24.3 g of magnesium fillings are suspended in 50 ml of anhydrous ethanol. 5 ml of carbon tetrachloride are added and, when the reaction has started, a mixture of 160 g of diethylmalonate, 100 ml of absolute ethanol and 400 ml of anhydrous ether is added dropwise, whereupon vigorous reflux is to be observed. After the reaction has subsided, the mixture is heated at the boiling point for a further 2 hours and cooled to −5° C. to −10° C. with dry ice/acetone, and a solution of 227.5 g of 2,4-dichloro-5-fluoro-benzoyl chloride (1) in 100 ml of absolute ether is slowly added dropwise at this temperature. The mixture is stirred at 0° C. to −5° C. for 1 hour and allowed to come to room temperature overnight, and a mixture of 400 ml of ice-water and 25 ml of concentrated sulphuric acid is run in, while cooling with ice. The phases are separated and subsequent extraction with ether is carried out twice. The combined ether solutions are washed with saturated NaCl solution and dried with $Na_2SO_4$ and the solvent is stripped off in vacuo. 349.5 g of diethyl 2,4-dichloro-5-fluoro-benzoyl-malonate (3) are obtained as the crude product.

0.15 g of p-toluenesulphonic acid is added to an emulsion of 34.9 g of crude diethyl 2,4-dichloro-5-fluoro-benzoyl-malonate (3) in 50 ml of water. The mixture is heated at the boiling point for 3 hours, while stirring thoroughly, the cooled emulsion is extracted several times with methylene chloride, the combined $CH_2Cl_2$ solutions are washed once with saturated NaCl solution and dried with $Na_2SO_4$ and the solvent is distilled off in vacuo. Fractionation of the residue in vacuo gives 21.8 g of ethyl 2,4-dichloro-5-fluoro-benzoyl-acetate (4) of boiling point 127° to 142° C./0.09 mbar.

A mixture of 21.1 g of ethyl 2,4-dichloro-5-fluoro-benzoyl-acetate (4), 16.65 g of ethyl o-formate and 18.55 g of acetic anhydride is heated at 150° C. for 2 hours. The volatile constituents are then distilled off under a waterpump vacuum, and finally under a fine vacuum at a bath temperature of 120° C. 25.2 g of crude ethyl 2-(2,4-dichloro-5-fluoro-benzoyl)-3-ethoxy-acrylate (5) remain. This product is sufficiently pure for the further reactions.

4.3 g of cyclopropylamine are added dropwise to a solution of 24.9 g of ethyl 2-(2,4-dichloro-5-fluorobenzoyl)-3-ethoxy-acrylate (5) in 80 ml of ethanol, while cooling with ice and stirring. When the exothermic reaction has subsided, stirring is continued at room temperature for a further hour, the solvent is stripped off in vacuo and the residue is recrystallized from cyclohexane/petroleum ether. 22.9 g of ethyl 2-(2,4-dichloro-5-fluoro-benzoyl)-3-cyclopropylamino-acrylate (6) of melting point 89° to 90° C. are obtained.

3.44 g of 80% pure sodium hydride are added in portions to a solution of 31.9 g of ethyl 2-(2,4-dichloro-5-fluoro-benzoyl)-3-cyclopropylamino-acrylate (6) in 100 ml of anhydrous dioxane, while cooling with ice and stirring. The mixture is then stirred at room temperature for 30 minutes and under reflux for 2 hours and the dioxane is stripped off in vacuo. The residue (40.3 g) is suspended in 150 ml of water, 6.65 g of potassium hydroxide are added and the mixture is refluxed for 1.5 hours. The warm solution is filtered and the residue is rinsed with $H_2O$. The filtrate is then acidified to pH 1–2 with half-concentrated hydrochloric acid, while cooling with ice, and the precipitate is filtered off with suction, washed with water and dried at 100° C. in vacuo. 27.7 g of 7-chloro-1-cyclopropyl-6-fluoro-1,4-dihydro-4-oxo-3-quinolinecarboxylic acid VIa of melting point 234° to 237° C. are obtained in this manner.

Example B

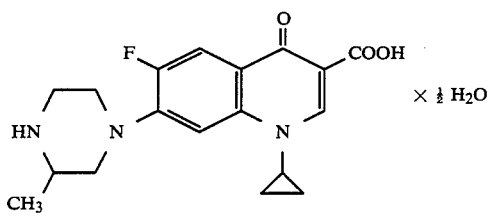

A mixture of 2.8 g (0.01 mole) of 7-chloro-1-cyclopropyl-6-fluoro-1,4-dihydro-4-oxo-3-quinolinecarboxylic acid and 5.1 g (0.051 mole) of 2-methylpiperazine in 6 ml of dimethylsulphoxide is heated at 140° C. for 2 hours. The solvent is then distilled off under a high vacuum, 6 ml of hot water are added to the residue and the mixture is kept at 95° C. for 1 hour. It is cooled with ice and the precipitate which has separated out is filtered off with suction, washed with a little water and dissolved in a mixture of 0.8 ml of acetic acid and 10 ml of water at 90° to 100° C. The filtrate is brought to pH 8 with potassium hydroxide solution (0.75 g of KOH in 0.7 ml of water) and the precipitate which has separated out is recrystallized from methanol. 1.8 g (52% of theory) of 1-cyclopropyl-6-fluoro-1,4-dihydro-4-oxo-7-(3-methyl-1-piperazinyl)-3-quinolinecarboxylic acid semihydrate of decomposition point 230° to 232° C. are obtained.

Example C

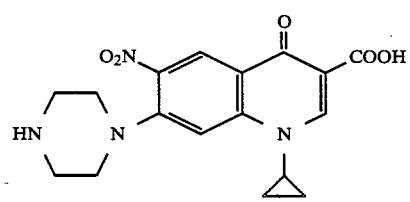

A mixture of 9.3 g (0.03 mole) of 7-chloro-1-cyclopropyl-1,4-dihydro-6-nitro-4-oxo-3-quinolinecarboxylic acid and 12.9 g (0.15 mole) of piperazine in 60 ml of dimethylsulphoxide is warmed at 120° C. for 15 minutes. After a short time, a precipitate separates out of the hot solution. The mixture is concentrated under a high vacuum, the residue is stirred with 30 ml of water and the mixture is heated again at 95° C. for 30 minutes. The mixture is adjusted to pH 8 with 2N hydrochloric acid and the precipitate is filtered off with suction and washed with water and methanol. 5.8 g (54% of theory) of 1-cyclopropyl-1,4-dihydro-6-nitro-4-oxo-7-(1-piperazinyl)-3-quinolinecarboxylic acid of decomposition point 296° to 298° C. are isolated.

Example D

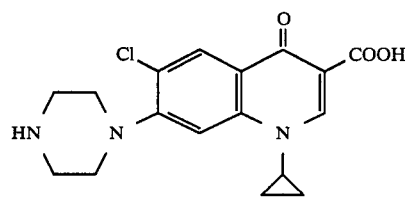

Analogously to Example C, 6,7-dichloro-1-cyclopropyl-1,4-dihydro-4-oxo-3-quinolinecarboxylic acid is converted into 1-cyclopropyl-6-chloro-1,4-dihydro-4-oxo-7-(1-piperazinyl)-3-quinolinecarboxylic acid of decomposition point 295° to 298° C.

Example E

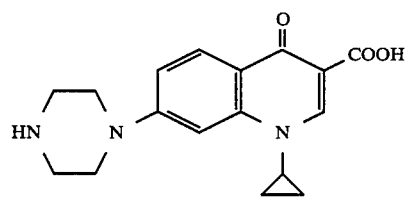

Analogously to Example C, 7-chloro-1-cyclopropyl-1,4-dihydro-4-oxo-3-quinolinecarboxylic acid is reacted with piperazine to give 1-cyclopropyl-1,4-dihydro-4-oxo-7-(1-piperazinyl)-3-quinolinecarboxylic acid of decomposition point 298° to 300° C.

End products

Example 1

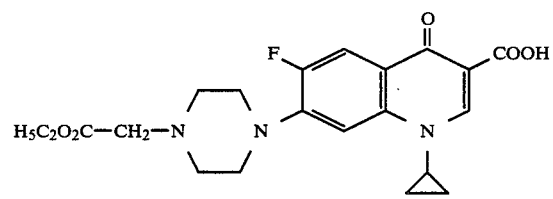

3.3 g (0.01 mol) of 1-cyclopropyl-6-fluoro-1,4-dihydro-4-oxo-7-(1-piperazinyl)-3-quinolinecarboxylic acid in 50 ml of dimethylformamide are heated at 90° C. with 2.5 g (0.015 mole) of ethyl bromoacetate, 1.2 g (0.02 mole) of triethylamine and 2.5 g of potassium iodide for 5 hours. The reaction mixture is poured into 30 ml of water and the precipitate is filtered off with suction, washed with water and recrystallized from methanol. 2.5 g of 1-cyclopropyl-6-fluoro-7-[4-(ethoxycarbonylmethyl)-1-piperazinyl]-1,4-dihydro-4-oxo-3-quinolinecarboxylic acid of melting point 192° to 194° C. are obtained.

The following compounds are obtained analogously to Example 1:

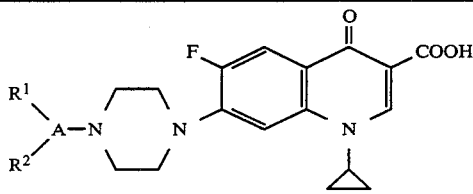

| Example | R¹<br>A—<br>R² | Melting point (°C.) |
|---|---|---|
| 2 | C₆H₅—CH₂O—CO—CH—<br>  \|<br>  C₆H₅ | 170 (decomposition) |
| 3 | H₂N—CO—CH₂— | 254 (decomposition) |
| 4 | NC—CH₂— | 166 (decomposition) |

Example 5

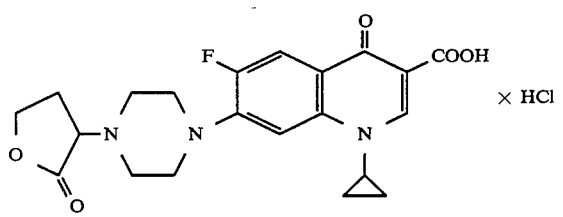

The procedure followed is analogous to Example 1, using α-bromobutyrolactone as the alkylating agent, and the reaction product is treated with dilute hydrochloric acid to give 1-cyclopropyl-6-fluoro-1,4-dihydro-4-oxo-7-[4-(2-oxo-tetrahydrofuryl-3)-1-piperazinyl]-3-quinolinecarboxylic acid hydrochloride of decomposition point 270° C.

Mass spectrum: m/e 415 (M+), 371, 342, 331, 301, 298, 289, 287, 275, 257, 245, 229 and 36 (100%, HCl).

Example 6

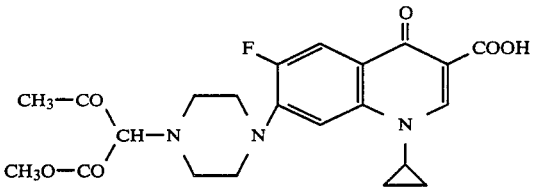

6.6 g (0.02 mole) of 1-cyclopropyl-6-fluoro-1,4-dihydro-4-oxo-7-(1-piperazinyl)-3-quinolinecarboxylic acid are heated at 80° C. with 4.5 g of methyl 2-chloroacetoacetate and 4.2 g of triethylamine in 100 ml of dimethylformamide for 3 hours. The solution is then concentrated in vacuo, the residue is stirred with 50 ml of water and the resulting solid product is washed with methanol and water and recrystallized from glycol monomethyl ether. 3.9 g (44% of theory) of 1-cyclopropyl-6-fluoro-1,4-dihydro-4-oxo-7-{4-[2-oxo-1-(methoxycarbonyl)-1-propyl]-1-piperazinyl}-3-quinolinecarboxylic acid of decomposition point 224° to 228° C. are isolated.

Example 7

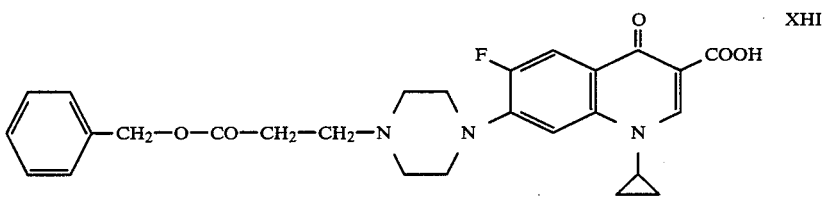

3.3 g (0.01 mole) of 1-cyclopropyl-6-fluoro-1,4-dihydro-4-oxo-7-(1-piperazinyl)-3-quinolinecarboxylic acid in 50 ml of dimethylformamide are heated at 70° to 80° C. with 5.8 g of benzyl 3-iodopropionate and 2.1 g of triethylamine for 2½ hours, while stirring. The solution is concentrated in vacuo, 30 ml of water are added and the pH is adjusted to 5. The precipitate is filtered off with suction and boiled up with methanol, 2.8 g of 7-[4-(2-benzyloxycarbonylethyl)-1-piperazinyl]-1-cyclopropyl-6-fluoro-1,4-dihydro-4-oxo-3-quinoline carboxylic acid hydriodide of decomposition point 206° to 210° C. being obtained.

The benzyl 3-iodopropionate used as the starting substance is obtained by the following route:

99 g of benzyl 3-chloropropionate are heated under reflux with 90 g of sodium iodide in 460 ml of acetone for 1 day. The reaction mixture is concentrated, 200 ml of methylene chloride are added and the mixture is washed with 3×100 ml of water. After drying with sodium sulphate, the mixture is concentrated and the residue is distilled under a high vacuum; yield: 91 g of benzyl 3-iodopropionate of boiling point 105° to 108°/0.1 mm.

Example 8

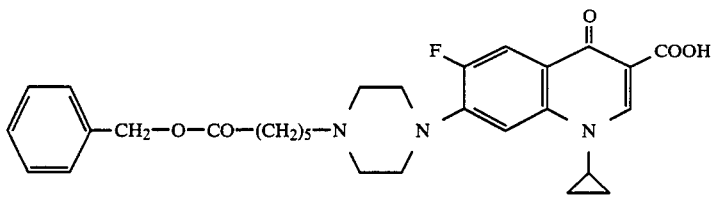

The procedure followed is analogous to Example 7, using benzyl 6-iodohexanoate, and 7-[4-(5-benzyloxycarbonylpentyl)-1-piperazinyl]-1-cyclopropyl-6-fluoro-1,4-dihydro-4-oxo-3-quinolinecarboxylic acid of melting point 176° to 178° C. is obtained.

The benzyl 6-iodohexanoate used as the starting substance is obtained by the following route:

46.5 g (0.3 mole) of 6-chlorohexanoic acid and 35.6 g of benzyl alcohol in 500 ml of toluene are heated in the presence of 1 g of p-toluenesulphonic acid, using a water separator. When the reaction has ended, the mixture is washed with 5% strength sodium bicarbonate solution and water, dried with sodium sulphate and concentrated and the residue is distilled, 61.5 g (85% of theory) of benzyl 6-chlorohexanoate of boiling point 163° to 165°/4 mm being obtained.

60 g (0.25 mole) of benzyl 6-chlorohexanoate are heated under reflux with 45 g of sodium iodide in 230 ml of acetone for 5 hours. The suspension is concentrated, 300 ml of methylene chloride are added and the mixture is washed with 2×200 ml of water. The organic phase is dried with sodium sulphate and concentrated and the residue is distilled in a bulb tube distillation apparatus. 63.8 g (77% of theory) of benzyl 6-iodohexanoate pass over at 220° to 230° C. (oven temperature)/0.4 mm.

Example 9

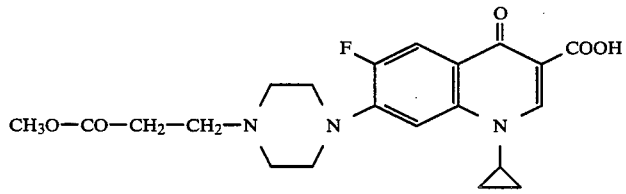

A mixture of 3.31 g (0.01 mole) of 1-cyclopropyl-6-fluoro-1,4-dihydro-4-oxo-7-(1-piperazinyl)-3-quinolinecarboxylic acid and 5 g (0.058 mole) of methyl acrylate in 50 ml of ethanol is heated under reflux for 2 hours. The solution is poured into 10 ml of water and the precipitate is filtered off with suction, washed with methanol and recrystallized from glycol monomethyl ether. 2.9 g (70% of theory) of 1-cyclopropyl-6-fluoro-1,4-dihydro-4-oxo-7-[4-(2-methoxycarbonylethyl)-1-piperazinyl]-3-quinolinecarboxylic acid of decomposition point 192° to 194° C. are obtained.

The following compounds are obtained analogously to Example 9:

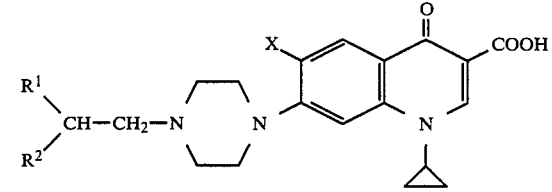

| Example | R¹ | R² | X | Melting point (°C.) |
|---|---|---|---|---|
| 10 | $C_2H_5O-CO-$ | H | F | 142 (decomp.) |
| 11 | $C_4H_9O-CO-$ | H | F | 141 (decomp.) |
| 12 | $C_6H_5-CH_2O-CO-$ | H | F | 140 |
| 13 | $CH_3O-CO-$ | H | Cl | 183 |
| 14 | CN | H | F | 255 (decomp.)(+) |
| 15 | CN | Cl | F | 202 (decomp.)(++) |
| 16 | $CH_3-SO_2-$ | H | F | 258 (decomp.) |

(+)According to the ¹H nuclear magnetic resonance spectrum, the 7-[4-(2-cyanoethyl)-1-piperazinyl]-1-cyclopropyl-6-fluoro-1,4-dihydro-4-oxo-3-quinolinecarboxylic acid present as a mixture with ~15% of 7-[4-(1-cyanoethyl)-1-piperazinyl]-1-cyclopropyl-6-fluoro-1,4-dihydro-4-oxo-3-quinolinecarboxylic acid.
(++)Mass spectrum: m/e 382 (M⁺—HCl), 338 (382-CO₂), 331, 289, 287, 245, 218, 154, 152, 44 (CO₂) and 36 (100%, HCl).

Example 17

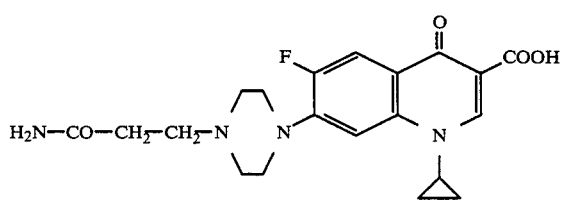

A mixture of 3.31 g (0.01 mole) of 1-cyclopropyl-6-fluoro-1,4-dihydro-4-oxo-7-(1-piperazinyl)-3-quinolinecarboxylic acid and 4.2 g (0.058 mole) of acrylamide in 50 ml of dimethylformamide is heated at 140° C. for 6 hours. The suspension is concentrated under a high vacuum and the residue is stirred with water and recrystallized from glycol monomethyl ether. 2 g (50% of theory) of 7-[4-(2-carbamoylethyl)-1-piperazinyl]-1-cyclopropyl-6-fluoro-1,4-dihydro-4-oxo-3-quinolinecarboxylic acid of decomposition point 283° to 286° C. are obtained.

Example 18

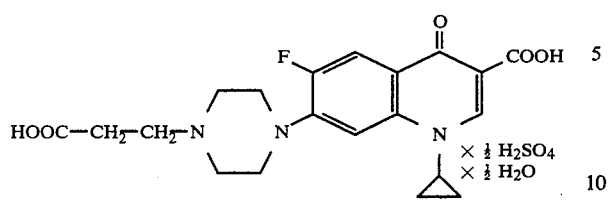

2.9 g of the compound from Example 9 are dissolved in a mixture of 14 ml of acetic acid and 9.5 ml of water, and 1.4 ml of concentrated sulphuric acid are added. The mixture is heated at 150° to 160° C. for 1.5 hours and poured into 90 ml of water. The precipitate is filtered off with suction, washed with water and methanol and dried. 2.3 g (72% of theory) of 7-[4-(2-carboxyethyl)-1-piperazinyl]-1-cyclopropyl-6-fluoro-1,4-dihydro-4-oxo-3-quinolinecarboxylic acid semisulphate semihydrate of decomposition point 258° to 261° C. are isolated.

$C_{20}H_{22}FN_3O_5 \cdot \frac{1}{2}H_2SO_4 \cdot \frac{1}{2}H_2O$ (461.4)

calculated: C: 52.06, H: 5.24, N: 9.11, S: 3.47, found: C: 51.7, H: 5.3, N: 9.1, S: 3.9.

The following compounds are obtained analogously to Example 12:

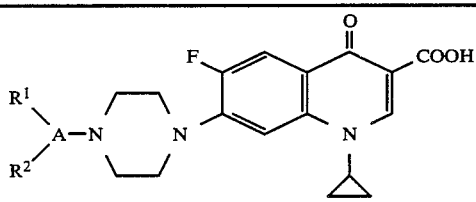

| Example | $R^1$<br>$\underset{R^2}{\diagdown}A-$ | | Melting point (°C.) |
|---|---|---|---|
| 19 | HOOC—CH₂— | × 2½ H₂O | 276 (decomp.)[1] |
| 20 | HOOC—(CH₂)₅— | × ½ H₂SO₄<br>× ½ H₂O | 254 (decomp.) |
| 21 | HOOC—CH—<br>│<br>C₆H₅ | × H₂O | 214 (decomp.)[2] |

[1] The reaction product (as the sulphate) was dissolved in dilute sodium hydroxide solution and precipitated at pH 5 as the betaine with dilute hydrochloric acid.
[2] The reaction mixture is poured onto water and adjusted to pH 4 with dilute sodium hydroxide solution, and the betaine is isolated.

Example 22

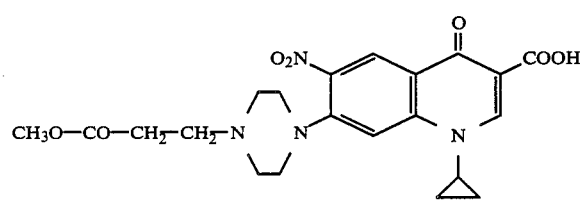

537 mg (0.0015) of 1-cyclopropyl-1,4-dihydro-6-nitro-4-oxo-7-(1-piperazinyl)-3-quinolinecarboxylic acid in a mixture of 7.5 ml of glycol monomethyl ether and 3 ml of dimethylsulphoxide are heated under reflux with 2 g of methyl acrylate for 8 hours. 10 ml of water are added to the solution and the precipitate is filtered off with suction, washed with methanol and dried. 0.5 g of 1-cyclopropyl-1,4-dihydro-7-[4-(2-methoxycarbonylethyl)-1-piperazinyl]-6-nitro-4-oxo-3-quinolinecarboxylic acid of decomposition point 208° to 211° C. are obtained.

Example 23

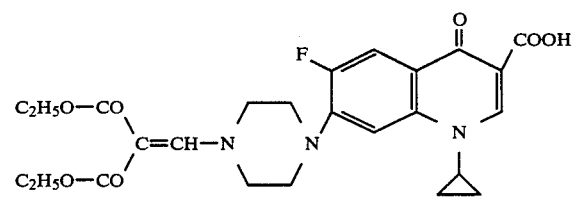

3.3 g of 1-cyclopropyl-6-fluoro-1,4-dihydro-4-oxo-7-(1-piperazinyl)-3-quinolinecarboxylic acid with 2.8 g of diethyl ethoxymethylenemalonate in a mixture of 0.4 g of sodium hydroxide in 5 ml of water and 25 ml of dioxane at room temperature for 5 hours. The mixture is left to stand overnight, a little insoluble material is filtered off and the filtrate is concentrated. The residue is taken up in about 30 ml of water, the pH is adjusted to 4 with dilute hydrochloric acid and the precipitate which has separated out is filtered off immediately, with suction, and washed with water. A greasy product which solidifies by stirring with isopropanol is obtained.

Yield: 2.4 g (48% of theory) of 1-cyclopropyl-7-[4-(2,2-diethoxycarbonyl-vinylene)-1-piperazinyl]-6-fluoro-1,4-dihydro-4-oxo-3-quinolinecarboxylic acid of decomposition point 184° to 188° C.

Example 24

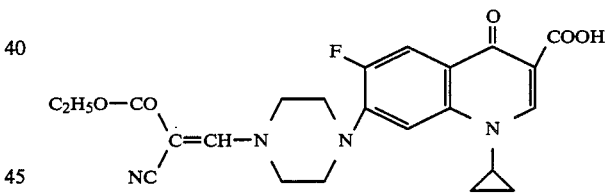

The procedure followed is analogous to Example 23, but using 2.2 g of ethyl ethoxymethylenecyanoacetate, and 2.35 g of 1-cyclopropyl-7-[4-(2-cyano-2-ethoxycarbonylvinylene)-1-piperazinyl]-6-fluoro-1,4-dihydro-4-oxo-3-quinolinecarboxylic acid of decomposition point 245° to 255° C. are obtained.

Example 25

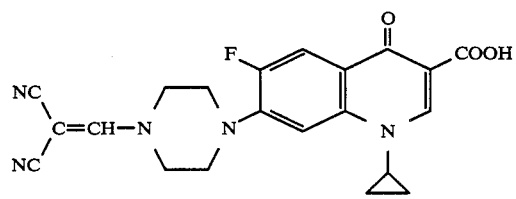

The procedure followed is analogous to Example 23, but using 1.6 g of ethoxymethylenemalonic acid dinitrile, and 4 g of 1-cyclopropyl-7-[4-(2,2-dicyanovinylene)-1-piperazinyl]-6-fluoro-1,4-dihydro-4-oxo-3- quinolinecarboxylic acid are obtained as a sparingly soluble product, which was washed with ethanol; decomposition point: 275° to 283° C.

Mass spectrum: m/e=363 (M+—$CO_2$), 362 (M+—COOH), 315, 287, 245 and 44 (100%, $CO_2$).

Example 26

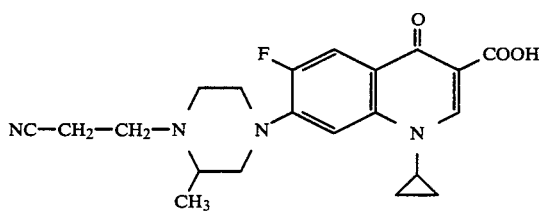

Analogously to Example 9, 3.45 g of 1-cyclopropyl-6-fluoro-1,4-dihydro-4-oxo-7-(3-methyl-1-piperazinyl)-3-quinolinecarboxylic acid (Example B) are reacted with 4.5 g of acrylonitrile to give 3 g of 7-[4-(2-cyanoethyl)-3-methyl-1-piperazinyl]-1-cyclopropyl-6-fluoro-1,4-dihydro-4-oxo-3-quinolinecarboxylic acid of melting point 203°–206° C.

$C_{21}H_{23}FN_4O_3$ (398.4): calculated: C: 63.3, H: 5.8, N: 14.1. found: C: 63.0, H: 5.9, N: 13.8.

USE EXAMPLES

The compound shown below is used as a comparison substance in the examples which follow:

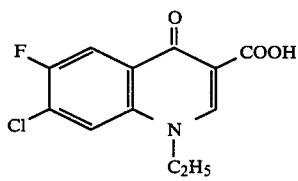

Example I

Xanthomonas oryzae test/bacteriosis/rice/systemic
Solvent: 48.5 parts by weight of dimethylformamide
Emulsifier: 1.5 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for systemic properties, standard soil in which young plants have been grown is watered with 100 ml of the preparation of active compound. 3 days after the treatment, the plants are inoculated with an aqueous suspension of Xanthomonas oryzae by pricking. Thereafter, the plants remain in a greenhouse at 24° to 26° C. and 70 to 80% relative atmospheric humidity for 14 days until they are evaluated.

In this test, Table A shows a clearly superior activity for the novel compounds compared with the prior art.

TABLE A

| Xanthomonas oryzae test/bacteriosis/rice/systemic | | |
|---|---|---|
| Active compounds | Amount applied in mg of active compound per 100 $cm^2$ | Disease infestation in % of the untreated control systemic |
| (structure 1) (known) | 10 | 60 |
| (structure 2) .HI | 10 | 40 |

Example II

Agar plate test
Nutrient medium used
  15 parts by weight of agar agar
  10 parts by weight of sucrose
  8 parts by weight of casein hydrolysate
  4 parts by weight of yeast extract
  2 parts by weight of dipotassium hydrogen phosphate
  0.3 parts by weight of magnesium phosphate are dissolved in 1,000 ml of distilled water and the solution is kept in an autoclave at 121° C. for 15 minutes.
Solvent: 10 parts by weight of dimethylformamide
Ratio of the amounts of solvent to nutrient medium: 0.2:99.8

To produce a suitable preparation of active compound, 1 part by weight of active compound is mixed with the stated amount of solvent.

The concentrate is thoroughly mixed, in the stated proportion, with the liquid nutrient medium and the mixture is then poured into Petri dishes.

When the nutrient medium has cooled and solidified, the plates are inoculated with the following microorganisms and are incubated at about 28° C.:

Evaluation is carried out after 2 days, the inhibition of growth being used as a measure of the action of the preparations.

In this test, Table B shows a clear superiority for the novel compounds compared with the prior art.

It is understood that the specification and examples are illustrative but not limitative of the present invention and that other embodiments within the spirit and scope of the invention will suggest themselves to those skilled in the art.

TABLE B

| Agar plate test Active compounds | Active compound concentration in ppm | Growth in figures of merit (1 = no growth, 9 = control) microorganisms | |
|---|---|---|---|
| | | *Agrobacterium tumefaciens* | *Corynebacterium michiganense* |
| 6-F, 7-Cl-1-ethyl-4-oxo-quinoline-3-carboxylic acid (known) | 10 | 4 | 4 |
| C$_6$H$_5$—CH$_2$—O—CO—CH$_2$—CH$_2$—N(piperazinyl)- on 7-position of 1-cyclopropyl-6-fluoro-4-oxo-quinoline-3-carboxylic acid | 10 | 3 | 2 |
| CH$_3$—O—CO—CH$_2$—CH$_2$—N(piperazinyl)- on 7-position of 1-cyclopropyl-6-fluoro-4-oxo-quinoline-3-carboxylic acid | 10 | 3 | 2 |
| NC—CH$_2$—CH$_2$—N(piperazinyl)- on 7-position of 1-cyclopropyl-6-fluoro-4-oxo-quinoline-3-carboxylic acid | 10 | 3 | 3 |
| C$_2$H$_5$O—CO—CH$_2$—CH$_2$—N(piperazinyl)- on 7-position of 1-cyclopropyl-6-fluoro-4-oxo-quinoline-3-carboxylic acid | 10 | 3 | 3 |
| CH$_3$—(CH$_2$)$_3$—O—CO—CH$_2$—CH$_2$—N(piperazinyl)- on 7-position of 1-cyclopropyl-6-fluoro-4-oxo-quinoline-3-carboxylic acid | 10 | 3 | 3 |
| C$_6$H$_5$—CH$_2$—O—CO—CH$_2$—CH$_2$—N(piperazinyl)- on 7-position of 1-cyclopropyl-6-fluoro-4-oxo-quinoline-3-carboxylic acid | 10 | 3 | 3 |

We claim:
1. A bactericidal composition comprising a diluent and a bactericidally effective amount of a heavy metal salt of a quinolinecarboxylic acid derivative of the formula

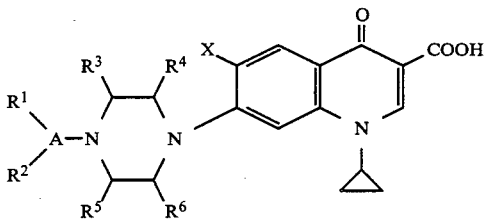

in which
- A represents straight-chain or branched alkylene with 1 to 6 carbon atoms or a >C=CH— radical,
- $R^1$ represents alkoxycarbonyl with 1 to 6 carbon atoms in the alkyl part, benzyloxycarbonyl, carboxyl, carbamoyl which is optionally substituted by 1 or 2 methyl or ethyl radicals, cyano or dialkoxyphosphonyl or alkylsulphonyl with 1 to 4 carbon atoms in the alkyl part and
- $R^2$ represents hydrogen, alkoxycarbonyl with 1 to 6 carbon atoms in the alkyl part, benzyloxycarbonyl, carbamoyl, cyano, chlorine, acetyl, alkyl with 1 to 3 carbon atoms or phenyl, or
- $R^1$ and $R^2$, together with the carbon atom which they substitute, can also form a 2-oxo-tetrahydrofuryl ring,
- $R^3$, $R^4$, $R^5$ and $R^6$ can be identical or different and represent hydrogen, methyl, ethyl or n- or i-propyl and
- X represents hydrogen, halogen or nitro.

2. A composition according to claim 1, wherein
- A represents straight-chain or branched alkylene with 1 to 5 carbon atoms or the >C=CH— group,
- $R^1$ represents alkoxycarbonyl with 1 to 5 carbon atoms in the alkyl part, benzyloxycarbonyl, carboxyl, carbamoyl which is optionally substituted by 1 or 2 methyl or ethyl radicals, cyano, methylsulphonyl or ethylsulphonyl, and
- $R^2$ represents hydrogen, alkoxycarbonyl with 1 to 5 carbon atoms in the alkyl part, benzyloxycarbonyl, carbamoyl, cyano, chlorine, acetyl, alkyl with 1 or 2 carbon atoms or phenyl, or
- $R^1$ and $R^2$ together with the carbon atom which they substitute, can also form a 2-oxo-tetrahydrofuryl ring,
- $R^3$, $R^4$, $R^5$ and $R^6$ represent hydrogen, methyl or ethyl and
- X represents hydrogen, fluorine, chlorine or nitro.

3. A composition according to claim 1, in which
- A represents straight-chain alkylene with 1 to 5 carbon atoms or the >C=CH— group,
- $R^1$ represents alkoxycarbonyl with 1 to 4 carbon atoms in the alkyl part, benzyloxycarbonyl, carboxyl, carbamoyl, cyano or methylsulphonyl and
- $R^2$ represents hydrogen, alkoxycarbonyl with 1 to 3 carbon atoms in the alkyl part, cyano, chlorine, acetyl or phenyl, or
- $R^1$ and $R^2$, together with the carbon atom which they substitute, can also form a 2-oxo-tetrahydro-3-furyl ring,
- $R^3$ represents hydrogen, methyl or ethyl,
- $R^4$ represents hydrogen,
- $R^5$ represents hydrogen or methyl,
- $R^6$ represents hydrogen and
- X represents hydrogen, fluorine, chlorine or nitro.

4. A composition according to claim 1, in which the heavy metal is zinc, manganese or copper.

5. A composition according to claim 1, wherein the quinoline carboxylic acid derivative is a heavy metal salt of
1-cyclopropyl-6-fluoro-1,4-dihydro-4-oxo-7-{4-[2-oxo-1-(methoxycarbonyl)-1-propyl]-1-piperazinyl}-3-quinolinecarboxylic acid,
7-[4-(2-benzyloxycarbonylethyl)-1-piperazinyl]-1-cyclopropyl-6-fluoro-1,4-dihydro-4-oxo-3-quinoline carboxylic acid,
1-cyclopropyl-6-fluoro-1,4-dihydro-4-oxo-7-[4-(2-methoxycarbonylethyl)-1-piperazinyl]-3-quinolinecarboxylic acid, or
1-cyclopropyl-7-[4-(2,2-diethoxycarbonyl-vinylene)-1-piperazinyl]-6-fluoro-1,4-dihydro-4-oxo-3-quinolinecarboxylic acid.

6. A method of combating plant-pathogenic bacteria, comprising applying to a plant, seed or site where a plant is to be grown a bactericidally effective amount of a 1-cyclopropyl-1,4-dihydro-4-oxo-3-quinolinecarboxylic acid derivative of the formula

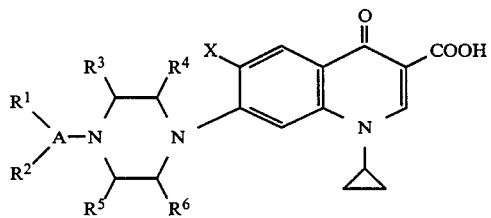

in which
- A represents straight-chain or branched alkylene with 1 to 6 carbon atoms or a >C=CH— radical,
- $R^1$ represents alkoxycarbonyl with 1 to 6 carbon atoms in the alkyl part, benzyloxycarbonyl, carboxyl, carbamoyl which is optionally substituted by 1 or 2 methyl or ethyl radicals, cyano or dialkoxyphosphonyl or alkylsulphonyl with 1 to 4 carbon atoms in the alkyl part, and
- $R^2$ represents hydrogen, alkoxycarbonyl with 1 to 6 carbon atoms in the alkyl part, benzyloxycarbonyl, carbamoyl, cyano, chlorine, acetyl, alkyl with 1 to 3 carbon atoms or phenyl, or
- $R^1$ and $R^2$, together with the carbon atom which they substitute, can also form a 2-oxo-tetrahydrofuryl ring,
- $R^3$, $R^4$, $R^5$ and $R^6$ can be identical or different and represent hydrogen, methyl, ethyl or n- or i-propyl and
- X represents hydrogen, halogen or nitro, or an acid addition salt, alkali metal salt, alkaline earth metal salt, heavy metal salt or hydrate thereof.

7. A method according to claim 6, in which
- A represents straight-chain or branched alkylene with 1 to 5 carbon atoms or the >C=CH— group,
- $R^1$ represents alkoxycarbonyl with 1 to 5 carbon atoms in the alkyl part, benzyloxycarbonyl, carboxyl, carbamoyl which is optionally substituted by 1 or 2 methyl or ethyl radicals, cyano, methylsulphonyl or ethylsulphonyl, and
- $R^2$ represents hydrogen, alkoxycarbonyl with 1 to 5 carbon atoms in the alkyl part, benzyloxycarbonyl, carbamoyl, cyano, chlorine, acetyl, alkyl with 1 or 2 carbon atoms or phenyl, or R¹ and R², together with the carbon atom which they substitute, can also form a 2-oxo-tetrahydrofuryl ring, R³, R⁴, R⁵ and R⁶ represent hydrogen, methyl or ethyl and X represents hydrogen, fluorine or nitro.

8. A method according to claim 6, in which

A represents straight-chain alkylene with 1 to 5 carbon atoms or the >C=CH— group, R¹ represents alkoxycarbonyl with 1 to 4 carbon atoms in the alkyl part, benzyloxycarbonyl, carboxyl, carbamoyl, cyano or methylsulphonyl, and R² represents hydrogen, alkoxycarbonyl with 1 to 3 carbon atoms in the alkyl part, cyano, chlorine, acetyl or phenyl, or R¹ and R², together with the carbon atom which they substitute, can also form a 2-oxo-tetrahydrofuryl ring, R³ represents hydrogen, methyl or ethyl, R⁴ represents hydrogen, R⁵ represents hydrogen or methyl, R⁶ represents hydrogen and X represents hydrogen, fluorine, chlorine or nitro.

9. A method according to claim 6, wherein the quinolinecarboxylic acid derivative is 1-cyclopropyl-6-fluoro-1,4-dihydro-4-oxo-7-{4-[2-oxo-1-(methoxycarbonyl)-1-propyl]-1-piperazinyl}-3-quinolinecarboxylic acid of the formula

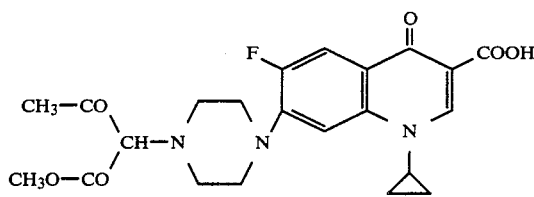

or an acid addition, alkali metal or alkaline earth metal salt, heavy metal salt or hydrate thereof.

10. A method according to claim 6, wherein the quinolinecarboxylic acid derivative is 7-[4-(2-benzyloxycarbonylethyl)-1-piperazinyl]-1-cyclopropyl-6-fluoro-1,4-dihydro-4-oxo-3-quinoline carboxylic acid of the formula

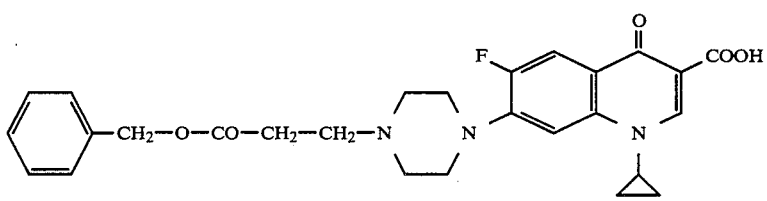

or an acid addition, alkali metal or alkaline earth metal salt, heavy metal salt or hydrate thereof.

11. A method according to claim 6, wherein the quinolinecarboxylic acid derivative is 1-cyclopropyl-6-fluoro-1,4-dihydro-4-oxo-7-[4-(2-methoxycarbonylethyl)-1-piperazinyl]-3-quinolinecarboxylic acid of the formula

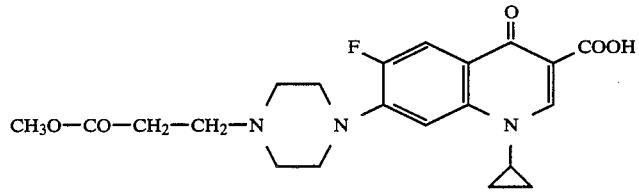

or an acid addition salt, alkali metal salt, alkaline earth metal salt, heavy metal salt or hydrate thereof.

12. A method according to claim 6, wherein the quinolinecarboxylic acid derivative is 1-cyclopropyl-7-[4-(2,2-diethoxycarbonyl-vinylene)-1-piperazinyl]-6-fluoro-1,4-dihydro-4-oxo-3-quinolinecarboxylic acid of the formula

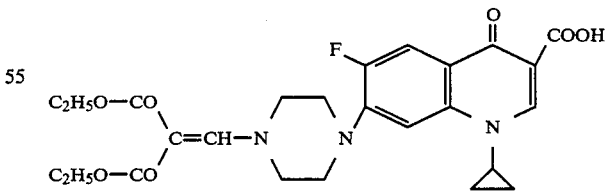

or an acid addition salt, alkali metal salt, alkaline earth metal salt, heavy metal salt or hydrate thereof.

* * * * *